(12) United States Patent
Rambod et al.

(10) Patent No.: US 8,376,947 B2
(45) Date of Patent: *Feb. 19, 2013

(54) APPLICATION OF IMAGE-BASED DYNAMIC ULTRASOUND SPECTROGRAPHY (IDUS) IN DETECTION AND LOCALIZATION OF BREAST MICROCALCIFCATION

(75) Inventors: Edmond Rambod, Los Angeles, CA (US); Yacov Itzchak, Ramat Efal (IL); Ari Shamiss, Yehud (IL); Daniel Weihs, Haifa (IL)

(73) Assignee: Bioquantetics, Inc., Los Angeles, CA (US)

( * ) Notice: Subject to any disclaimer, the term of this patent is extended or adjusted under 35 U.S.C. 154(b) by 1353 days.

This patent is subject to a terminal disclaimer.

(21) Appl. No.: 12/079,272

(22) Filed: Mar. 26, 2008

(65) Prior Publication Data
US 2009/0247869 A1  Oct. 1, 2009

(51) Int. Cl.
*A61B 8/00* (2006.01)
(52) U.S. Cl. ........ 600/437; 600/407; 600/424; 600/430; 600/443; 600/438; 382/131
(58) Field of Classification Search .................. 600/407, 600/424, 430, 437, 438, 441, 443; 382/131; 601/2
See application file for complete search history.

(56) References Cited

U.S. PATENT DOCUMENTS

| | | | |
|---|---|---|---|
| 5,749,364 A | 5/1998 | Siwa, Jr. et al. | |
| 6,061,589 A * | 5/2000 | Bridges et al. | 600/430 |
| 6,728,567 B2 | 4/2004 | Rather et al. | |
| 7,149,566 B2 | 12/2006 | Lee | |
| 7,647,089 B2 * | 1/2010 | Bond et al. | 600/430 |
| 7,806,828 B2 | 10/2010 | Stringer | |
| 8,043,217 B1 * | 10/2011 | Rambod | 600/438 |
| 8,050,740 B2 * | 11/2011 | Davis et al. | 600/430 |
| 8,109,878 B1 * | 2/2012 | O'Ruanaidh et al. | 600/443 |
| 8,200,313 B1 * | 6/2012 | Rambod et al. | 600/424 |
| 2003/0220556 A1 * | 11/2003 | Porat et al. | 600/407 |
| 2005/0220711 A1 * | 10/2005 | Katz | 424/9.5 |
| 2006/0241455 A1 | 10/2006 | Shvarts | |
| 2011/0044524 A1 * | 2/2011 | Wang et al. | 382/131 |
| 2011/0130660 A1 * | 6/2011 | Cloutier et al. | 600/438 |

* cited by examiner

*Primary Examiner* — Tse Chen
*Assistant Examiner* — Baisakhi Roy
(74) *Attorney, Agent, or Firm* — Thomas I. Rozsa

(57) ABSTRACT

A method for the detection and localization of breast microcalcification through a precise method of ultrasound impacting and ultrasound frequency wave detection which will enable the system to detect not only if there is a microcalcification in the breast, but the precise location of the microcalcification and the mass of the microcalcification. The invention is also a method and system that provides bi-modal guided stimulation of a targeted mass within the breast to determine the location and nature of the microcalcification within the breast.

33 Claims, 7 Drawing Sheets

IDUS™ - The Principle

FIG. 1: IDUS™ - The Principle

FIG. 2: IDUS™ - The Sequence

FIG. 3: IDUS™ - System Components

FIG. 4: IDUS™ - Flow Diagram

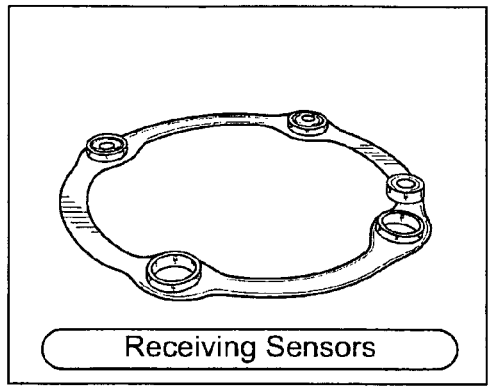
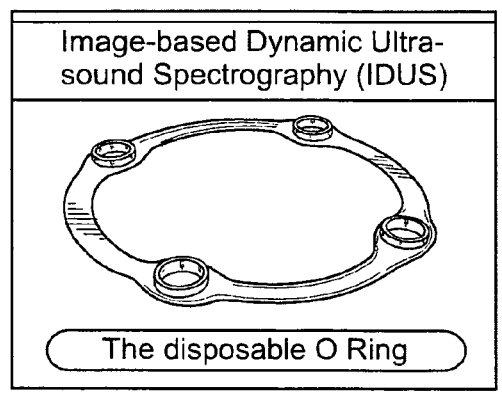
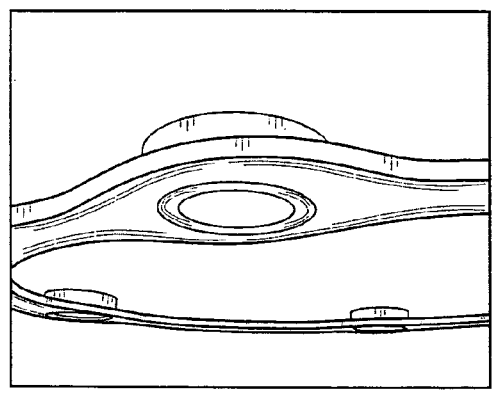
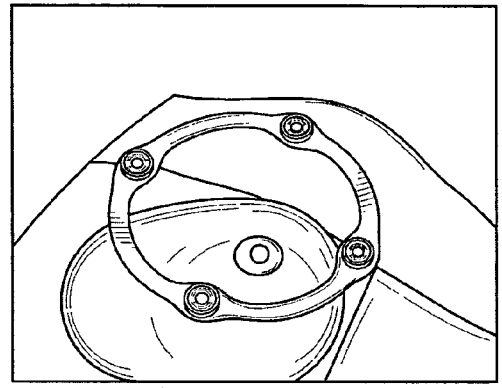
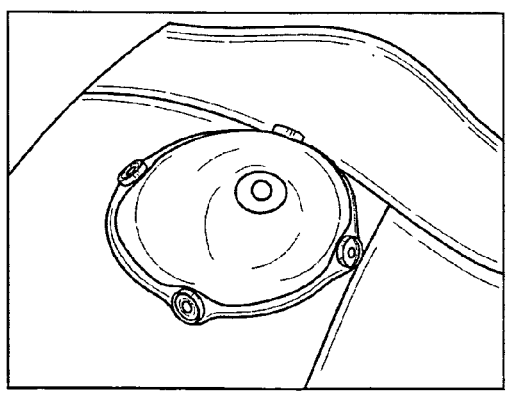
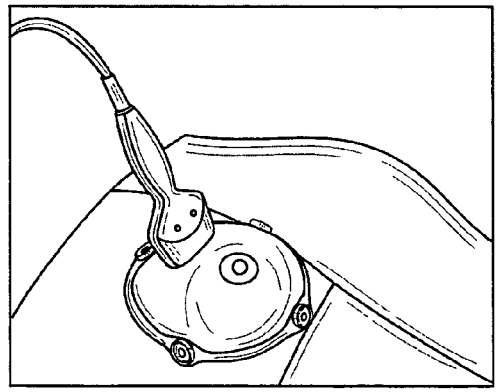
FIG. 5

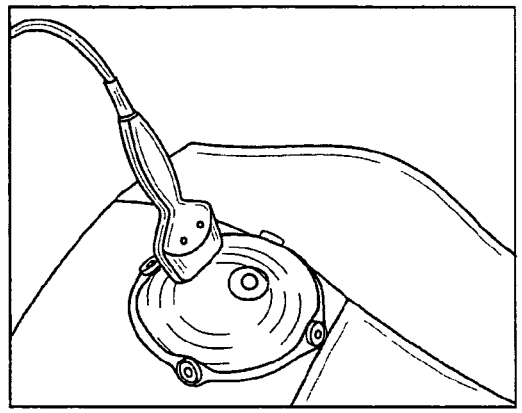
G
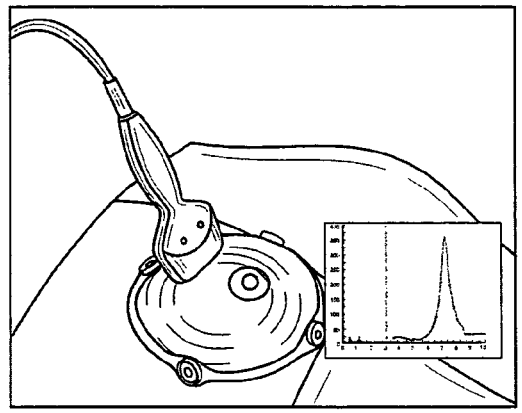
H
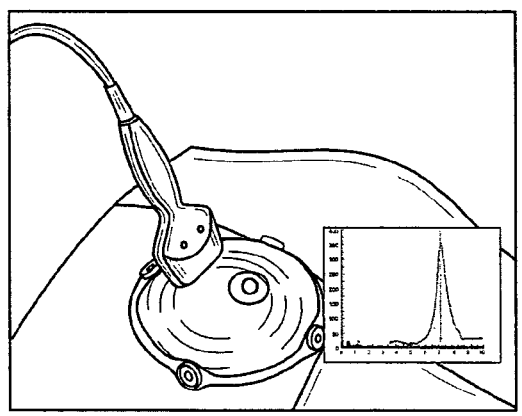
I
FIG. 5

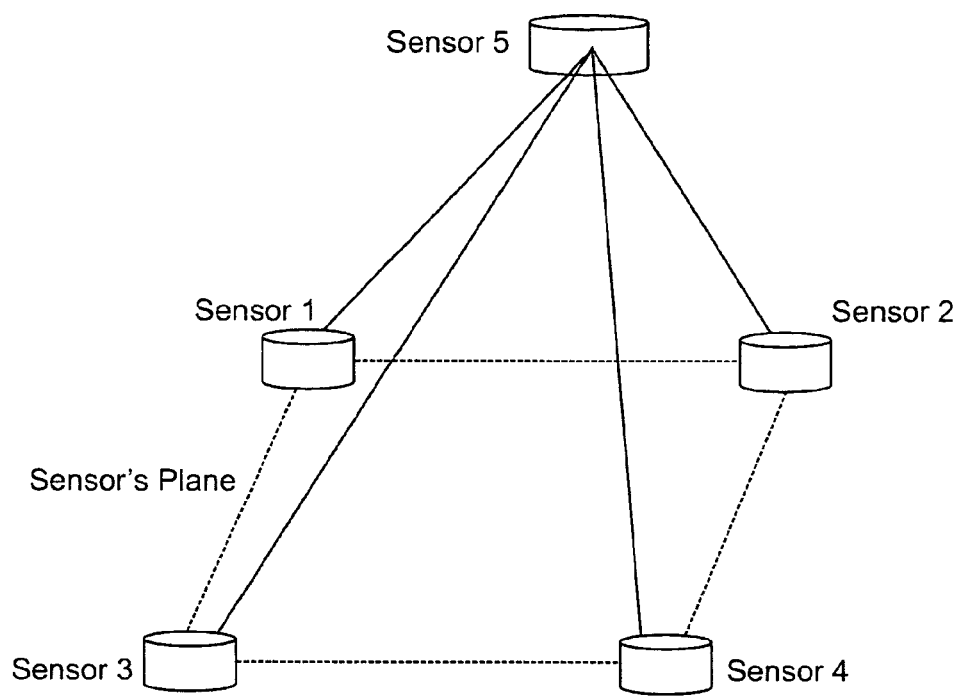
Figure 6A: Schematics of the relative locations of the five receiving sensors.
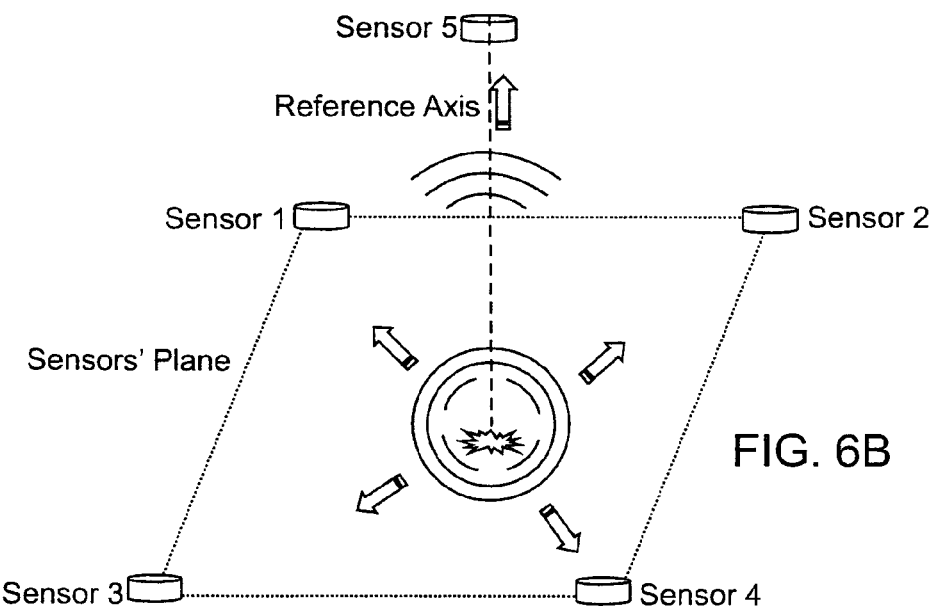
Figure 6B: Schematics of the signal from the target received by the receiving sensors.

APPLICATION OF IMAGE-BASED DYNAMIC ULTRASOUND SPECTROGRAPHY (IDUS) IN DETECTION AND LOCALIZATION OF BREAST MICROCALCIFCATION

BACKGROUND OF THE INVENTION

1. Field of the Invention

The present invention relates to the diagnosis of medical conditions and in particular to medical diagnosis of abnormalities within a female breast which is performed through the use of non-invasive ultrasound techniques to determine whether or not there is any microcalcification in a female breast and further, to determine the location where the microcalcification is located as well as the size of the microcalcification.

2. Description of the Prior Art

In general, breast screening for cancer and microcalcification detection have been performed using different imaging modalities in the prior art and there are several techniques that are currently in active use. The techniques are as follows:

X-Ray Mammography

To date, X-ray mammography is the method of choice and the "gold standard" for breast screening and diagnosis with which other technologies are compared. In order to perform this test a breast is exposed to an X-ray beam whose transmission is measured. The breast is rather strongly compressed between an X-ray sensitive screen and a transparent plate to:

Obtain a uniform thickness,

Reduce the total thickness in order to facilitate operation in the range of lower photon energy levels and higher contrast between tissues, to obtain a clearer image, and Reduce overlapping of the different inner breast tissues to increase clarity of the image and better sensitivity.

X-ray mammography was first pioneered by Warren in 1930 but it has been widely used only for the last 30 years. The identification of a breast lesion relies on the imaging of radiographic density changes caused by the lesion and associated changes in breast architecture, vascularity or skin contour. Radiographically, benign lesions are usually less dense than those that are malignant, and in general they have smooth outlines. Malignant lesions, on the other hand, have irregular outlines. When the breast is glandular it is more difficult to image its architecture than when the breast contains large amounts of fat. The breast might be so radiographically dense that breast structure cannot be imaged with sufficient clarity to identify a discrete mass. In the fatty breast the tumor may be clearly visible, as well as changes in vascularity and skin contour. Although, larger tumor in a dense breast can be seen less clearly, it may be identifiable by micro-calcifications. In vivo radiographic studies on the incidence of micro-calcifications show that they can be detected in 40% to 50% of malignant tumors and in about 20% of benign tumors, and histological sections show even higher percentages. Several randomized controlled studies undertaken in different countries to assess the value of screening mammography have demonstrated a clear benefit of screening mammography for women over age 50 or even over the age of 40 in some countries. Although the results for women younger than age 50 are still controversial.

During the last fifteen years, mammography screening has reduced the mortality rate among women with breast cancer considerably[1], by detecting approximately 85% to 90% of breast cancers. The reported sensitivity of X-ray mammography varies from 83% to 95%. The reported specificity of X-ray mammography varies from 90% to 98%. However, the reported positive predictive value (PPV) which includes the prevalence of detecting the disease is quite poor, varying from 10% to 50%.

[1] "Preventing Chronic Diseases: Investing Wisely in Health Screening to Prevent Cancer Deaths", U.S. Department of Health and Human Services.

In many developed countries, the film-screen mammography (FSM) is being gradually replaced by full-field digital mammography (FFDM) which is identical to FSM except for the electronic detector that captures and facilitates display of the X-ray signals on a computer or laser-printed film. Although the resolution of the new FFDM instruments is not higher than the traditional FSM technique, additional data processing may help to find tumor marks with higher accuracy.

Two and Three Dimensional Ultrasound Imaging

Conventional ultrasound imaging utilizes megahertz frequency sound waves which reflect at boundaries between tissue with different acoustic impedance, which is the product of the penetrating sound velocity and material density. The time interval of arrival of these reflections is proportional to the depth of field (boundaries of a targeted area). Thus, ultrasound can map acoustic tissue boundaries.

Traditionally, 2-dimensional ultrasound imaging is used as an adjunct to X-ray mammography in the identification and differentiation of cysts or solid masses. Ultrasound imaging of the breast may also help radiologists to evaluate some lumps that can be felt but that are difficult to see on X-ray mammogram, especially in dense breast or implants. It is also in wide use in guided biopsy since it allows real time imaging of the breast. 3-Dimensional ultrasound imaging is seldom used in breast screening due to very limited added information.

Evaluation of the ultrasound technique in distinguishing malignant from benign tumors has shown the accuracy of benign condition detection to be 99.5%. Reportedly, a combination of ultrasonography and standard X-ray mammography has yielded a sensitivity of 92% and a specificity of 98%. With recent advancements in ultrasound platforms, some earlier-stage, clinically occult tumors, that were missed by screening mammography, could be detected. Since the speed of sound in fatty and less fatty breast tissues are approximately the same, ultrasound possesses a promising role in the future screening of younger women with dense breast and high risk factors. However, traditional ultrasound has poor calcification detectability.

Magnetic Resonance Imaging (MRI)

MR images are created by recording the signals generated after radiofrequency excitation of hydrogen nuclei (or other elements) in tissue exposed to a strong static magnetic field. The signals have characteristics that vary according to the tissue type (fat, muscle, fibrotic tissue, etc.).

The method has minimal hazards from magnetic field effects and does not use ionizing radiation. The first MRI results of the human breast were disappointing, but subsequent use of an intravenous gadolinium based contrast agent has offered a clear advance and increased sensitivity. Reportedly, the sensitivity of contrast-enhanced MRI in detection of suspicious breast lesions varies from 88% to 100% (average reported sensitivity of about 95%). However the specificity of the contrast-enhanced MRI has been quoted as rather variable, ranging from 37% to 100%. This is mainly because of considerable exceptions and overlaps in contrast agent uptake and kinetics between benign and malignant tumors. The prevalence of cancer by MRI screening in high risk women is significantly greater than that reported in a similar population screened by ultrasound (4% vs. 1.3%)[2]. However, neither the technique nor the interpretive criteria are standardized as of to date, leading to variability in performance and in results interpretation. In addition, MRI can only be performed in a setting in which it is possible to perform biopsy of lesions detected solely by MRI.

[2] E. A. Morris, L. Liberman, D. J. Ballow et al. 2003 "MRI of Occult Breast Carceonoma in a high risk population", *ARJ* 2003; 181:619-626.

Despite its high accuracy in detecting malignancies in breast, MRI is not recommended as a routine examination for the differentiation of benign and malignant lesions/tumors. MRI is a prohibitively expensive modality and it is unsuitable for large-scale screening programs. A US survey conducted by market research firm IVM has revealed that not more than 17% of US imaging facilities provide MRI imaging on site. Nonetheless, where available, MRI can be used as a complementary methodology to assist in differential diagnosis of uncertain lesions.

Positron Emission Tomography (PET) Scan

To conduct a PET scan, a short-lived radioactive tracer isotope, which decays by emitting a positron (chemically incorporated into a metabolically active molecule), is injected into the blood circulation. There is a waiting period while the metabolically active molecule becomes concentrated in tissues of interest; then the patient is placed in the imaging scanner where the positron encounters an electron, producing a pair of photons moving in almost opposite directions. These are detected when they reach a sensitive material in the scanning device, creating a burst of light which is detected by photomultiplier tubes.

Optical Mammography and Spectroscopy of Breast

In the past decade, optical imaging techniques using near-infrared light (NIR) have attracted considerable interest. Characterization, differentiation and localization of different lesions are possible due to the presence of optical absorption contrast between tumors and healthy tissues due to an increased hemoglobin concentration as a result of angiogenesis. The hemoglobin oxygen saturation of suspicious sites can be reconstructed by spectroscopic analysis and can additionally serve as a criterion for diagnosing malignancies. Optical imaging techniques incorporate detection of photons that propagate through the breast with light propagation models to reconstruct the optical properties of the illuminated tissue. By altering the wavelength of the optical source, the spectroscopic dependence of optical properties can be obtained.

An early trans-illumination platform for breast lesion detection demonstrated low sensitivity, specificity and reproducibility. The optical imaging techniques can be split into three groups:

Continuous wave (CW)
Time-domain
Frequency-domain

Each group has its own strengths and weaknesses. Optical imaging techniques have some advantages and drawbacks. The notable advantages are that they:

Are relatively inexpensive
Use NIR and do not impose ionizing radiation
Have potential for portability The major drawback associated with optical imaging remains light propagation in biological tissue, which is highly scattered, resulting in poor resolution. Improving spatial resolution and discriminating between absorption and scattering remain the biggest challenges that are faced by optical imaging.

Optical mammography has yet to demonstrate its potential to be a stand-alone imaging modality, mainly because of its poor specificity and sensitivity. Nevertheless, it may supplement existing breast imaging techniques by characterizing lesions in suspicious cases, resulting in a reduction of the number of unnecessary biopsies.

Thermo/Photo-Acoustic Breast Imaging

Thermo-acoustics exposes the breast to short pulses of externally applied electromagnetic energy. Differential absorption induces differential heating of the tissue followed by rapid thermal expansion. This generates sound waves that are detected by acoustic transducers positioned around the breast. Tissues that absorb more energy expand more and produce higher amplitude sound waves. The time-of-flight, amplitude and duration of acoustic pulses recorded on the tissue surface possess information regarding the location, absorption and dimensions of the source, thereby permitting a 3-dimensional reconstruction of the targeted absorber.

When the incident electromagnetic energy is visible or NIR light, the term "photo-acoustics" is used instead of thermo-acoustics. Photo-acoustics combines the advantages of two techniques. First, like optical mammography, photo-acoustics probes the optical contrast of the tumor site with respect to surrounding tissue. Secondly, all information about optical absorption inhomogeneities is carried to the breast surface by ultrasound waves which have low attenuation and scattering in soft tissue and thus, resulting in poor sensitivity. Similar to thermo-acoustic techniques, photo-acoustics retain 3-dimensional structural information of the targeted area.

One of the major disadvantages of these techniques is the difficulties in displaying and analyzing the 3-dimensional information retained from the targeted area. Therefore, the time and cost required for image retrieval and analysis of the thermo/photo-acoustic techniques are potentially greater when compared with that of X-ray mammography and ultrasound. Moreover, these techniques have yet to demonstrate reproducibility, adequate sensitivity, specificity and practicality.

A summary of the prior art which will be more understandable after the detailed description of the preferred embodiment is set forth in Table 1 which compares the present invention IDUS technology with leading diagnostic imaging modalities. Also, reference is made to Table 2 at the end of the detailed description of the preferred embodiment which sets forth competing imaging technologies and the strengths and weaknesses of competing imaging technologies as compared with the present invention IDUS system.

There is a significant need for an improved method which will be able to determine not only whether a microcalcification is present in the female breast, but also be able to evaluate the size the location of the microcalcification and through a preset series of information, determine and evaluate whether or not the microcalcification is possibly malignant which would result in further medical treatment and biopsy to remove the microcalcification.

SUMMARY OF THE INVENTION

The present invention is based on the utilization of externally produced, noninvasive image-based dynamic ultrasound spectrography for real-time imaging and stimulation of breast microcalcification masses which can be under 100 microns in size and confined within the breast tissue. The purpose of this design is to: 1) detect and 2) determine the three-dimensional positioning of the microcalcification areas within the breast in vivo for follow-ups and guidance of various medical procedures.

It has been discovered, according to the present invention, that the improved technique to locate the microcalcification includes the utilization of a disposable complaint O-ring which is designed to be placed around the breast, leaving the center portion available for an ultrasound scanner.

It has further been discovered, according to the present invention, that in the preferred embodiment, four round reusable sensors (receivers) are firmly housed at 90 degrees apart on the O-ring. Three of the sensors would determine the X-Y-Z coordinates of the exact location of the microcalcification within the breast. The forth sensor is used for correcting any errors in determining the X-Y-Z coordinates by the other three sensors. Another such sensor is positioned within the imaging scanner and used to provide a reference vertical axis to: 1) determine the depth of the microcalcification sites and 2) relative to which the said X-Y-Z coordinates are determined. In the present invention, this vertical axis is important to ensure that the positioning of microcalcification within the breast is performed irrespective of the geometry changes that may occur in the breast at different times and between one examination to the other.

It has also been discovered, according to the present invention, that once the disposable ring and the housed sensors are positioned around the breast, an ultrasound transducer (scanner) will then scan of the breast with a 1-14 Megahertz carrier frequency, looking for the areas of interest with potential microcalcification. Once an area of interest (AOI) is located, the scanner will remain steady on the breast, the imaging mode of the said Image-based Dynamic Ultrasound Spectrograph (IDUS) device is turned off and the stimulation mode of the said device is activated. The area of interest will then be stimulated by a swept band of modulated frequencies at a given range corresponding to the response frequency of said microcalcifications. When microcalcification is present, it will be stimulated by the sequential modulated frequency schemes of the present invention resulting in a characteristic response proportional to its mass density and shape. The response will be monitored and recorded in real time and will appear as a spectrum where the peak frequency will be recorded and spectrally analyzed. The recorded peak frequency will then be compared in real-time with a predetermined database of frequencies which will provide information as to what specific microcalcification size the frequency corresponds to based on a predetermined map of frequencies corresponding to specific microcalcification masses. A pre-programmed color-coded scheme will then be applied to color the site with detected microcalcification where different microcalcification masses will be colored differently according to the color-coded scheme.

It has further been discovered that emitted frequencies from the targeted soft tissue is estimated at few Hertz (1-50 Hz), whereas corresponding emitted frequencies from a micro-calcification sites are estimated to be in the range of 100 Hz to one KHz. It has also been discovered according to the present invention that the modulated frequency band used to stimulate the microcalcification sites is not in the range that can stimulate the soft tissue and therefore, the sites with microcalcification are distinguished by a unique set of frequencies from the surrounding tissue.

It has further been discovered, according to the present invention, that utilizing specialized localization methodology the exact three-dimensional position of the area of interest with microcalcification is determined based on the signals received by the receiving sensors and analyzed respectively. The exact three-dimensional position of the targeted area will be displayed on the B-mode image and marked for future reference and follow up.

It is an object of the present invention to provide a method for the detection and localization of breast microcalcification through a precise method of ultrasound impacting and ultrasound frequency wave detection which will enable the system to detect not only if there is a microcalcification in the breast, but the precise location of the microcalcification and the mass of the microcalcification.

It is a further object of the present invention to provide a method and system that provides bi-modal image guided stimulation of a targeted mass within the breast to determine the location and nature of the microcalcification within the breast.

It is a further object of the present invention to provide real time qualitative imaging of the targeted area and quantitative data about the mass structural of the targeted area.

It is also an object of the present invention to provide a methodology to locate microcalcification and determine the nature of the microcalcification without providing the drawbacks of other imaging and screening modalities such as being invasive, having no ionization radiation, being safe, reliable, cost-effective, not Doppler based, not angular-dependent and being portable, suitable for field applications and suitable for operating room conditions.

It is a further object of the present invention to provide a pre-determined series of frequency map information which is programmed into the system so that once a specific microcalcification site is located and once its peak response frequency is determined, the peak response frequency can be compared to a preset series of mapped frequencies for correlative detection and site identification.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 5 in general illustrates the application of the technology in the present invention;

FIG. 5A is a perspective view of the disposable O-ring with four spaced apart housing for the receiving sensors;

FIG. 5B is an exploded view showing the O-rings with the specific receiving sensors positioned on the O-ring;

FIG. 5C is a bottom perspective view of the O-ring illustrating a receiving sensor within the O-ring and also illustrating the thin transparent film underneath the sensor separating it from contacting the skin;

FIG. 5D is an exploded view showing the disposable O-ring with the receiving sensors in place located above the breast before it is positioned on a breast;

FIG. 5E is a perspective view showing the disposable O-ring and the receiving sensors positioned on the breast contacting the skin;

FIG. 5F is a perspective view showing the disposable O-ring and the receiving sensors positioned on the breast and an ultrasound scanner scanning the breast;

FIG. 5G is a perspective view showing the device in its stimulation mode and stimulating signals transmitted by the ultrasound B-mode scanner towards the area of interest;

FIG. 5H is a perspective view showing the ultrasound scanner transmitting sweeping frequencies in search for a peak response frequency from the area of interest. The disposable O-ring is attached to the breast and the receiving sensors sense the response frequencies emanating from the area of interest. The detected response frequency will reach a peak when an area with microcalcification of certain mass is detected;

FIG. 5I shows that the recorded response frequency reaches a peak indicating an area with certain microcalcification mass detected within the breast. The detected area of microcalcification is then marked on the B-mode image according to a pre-defined color-code scheme and subsequently, the exact three-dimensional position of the area with micro-calcification is determined and marked on the B-mode image and recorded for future follow ups; and FIG. 6A shows the schematics of the relative locations of the five receiving sensors. Four sensors are positioned around the O-ring wherein the fifth one is embedded within the transmitting transducer and provide a reference axis relative to the other four receiving sensors.

FIG. 6B shows the schematics of the signal from the target received by the receiving sensors. The stimulated target emanates response frequency signals to all directions. The four receiving sensors determine the 3-D position of the target wherein the fifth one provides a reference axis to the target. This reference axis is used to refer the position of any detected target at any point of time to any future examination on the same subject. This will enable the technique to be used over different periods of time to examine the same targeted area.

DETAILED DESCRIPTION OF THE PREFERRED EMBODIMENTS

Figure 1:
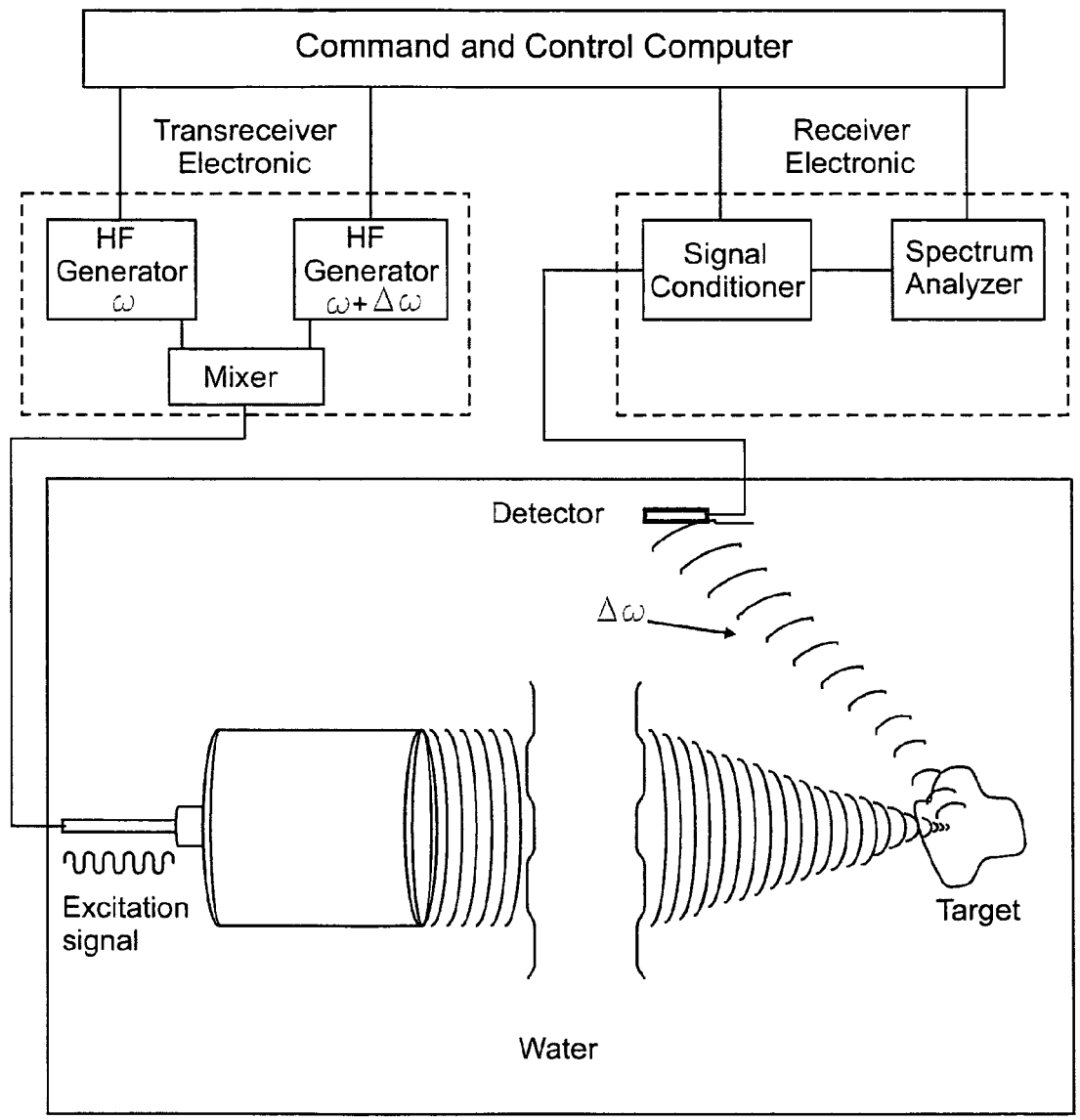
FIG. 1 is a schematic diagram of the present invention IDUS technology demonstrating the insonification procedure imposing by the modulated ultrasound frequency on a target and the detection and analysis methodology of the response frequencies emanating from the target.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The fundamental concept of the present invention is depicted in the enclosed FIG. 1 which is a schematic representation of the present invention as described below.

The invention for the noninvasive remote ultrasound detection and localization of the targeted breast microcalcification masses by sensing their emanating acoustic response is based on the insonification of the breast areas with microcalcification masses with two or more sweeping ultrasound waves differing slightly in frequency, to result in application of a sweeping low frequency (Hertz or kilohertz) acoustic force, at the microcalcification areas. This low frequency radiation force will stimulate the microcalcification masses and instigate their vibration at frequencies typical of their masses, generating unique signatures. The vibrational response of the microcalcification which is related to the difference of the two or more transmitted ultrasound frequencies (low frequency modulation), is measured by an array of noninvasive remote low frequency (Hz or kHz) acoustic detectors. This measurement allows for the evaluation of the acoustic signatures according to a pre-defined frequency signature map corresponding to different masses of microcalcification, thus providing information on the 3-dimensional real-time positioning of the microcalcification areas within the breast tissue within the body. This technique involves two main components:

(i) The aiming high frequency ultrasound scanner and insonifiers, and (ii) The wide angle, low frequency array of acoustic detectors/receivers.

Ultrasound radiation modalities have a very small wavelength, to demonstrate the necessary spatial resolution for exact targeting of the interrogated breast microcalcification areas. Generally, it is well known in the art that many rigid structures, especially those characterized by distinguished vibratory mass, shapes and materials, manifest acoustic natural resonances at particular frequencies, which can serve as their acoustic signatures. The acoustic signature is strongly dependent on the structure, density and material strain coefficients and the targeted areas relative to the surrounding environment. These resonances can be experimentally measured by the excitation of the modes of vibrations and listening to the radiated acoustic waves by known listening devices, like our ears, microphones, accelerometers, etc. Additionally, such acoustic resonances can be theoretically predicted using different computer programs, like the Finite Elements Method.

The present invention remotely measures the characteristic acoustic signature/s of the micro-calcification areas/masses, using high frequency ultrasound (1-14 MHz), which is well known to be able to penetrate the human body (skin, fat, muscle, etc) and image the area of interest with high precision. By interrogating the imaged areas of interest, characteristic response frequencies will be recorded if microcalcification is present. Real-time detection and analysis of the emitted acoustic response signature from an area with microcalcification by a single detector/receiver can provide a single dimension position of the targeted area. Time-of-Flight and other triangulation techniques are used, with at least three receivers positioned such as to obtain the three-dimensional real-time position of the targeted area. The advantage of this invention is in its spatial resolution, which is independent of the ultrasound imaging resolution and ultrasound imaging capabilities which is safe compared to other X-ray-based imaging modalities.

Image-Based Dynamic Ultrasound Spectrography—The Rationale

The Image-based Dynamic Ultrasound Spectrography (IDUS) has already been shown to provide a real-time, safe, reliable and cost-effective diagnostic technique for detection of structural flaws in implanted medical devices. The fundamental concept of Image-based Dynamic Ultrasound Spectrography (IDUS) is to excite the target externally and then measure its response by using specialized sensor/s. By measuring the emanating response of the target, its structural state can be determined relative to the surrounding environment.

Image-Based Dynamic Ultrasound Spectrography (IDUS)—The Principle

Image-based Dynamic Ultrasound Spectrography (IDUS) is an active acoustic technology in which the targeted site is imaged first and then stimulated using proprietary and specialize sequential schemes delivered by the same ultrasound imaging transducer (see FIG. 1). The frequency response of the resulting stimuli is detected by a detector or a series of detectors positioned externally on the body and in the immediate vicinity of the transmitting transducer, and spectrally analyzed in real-time using proprietary algorithm.

Image-Based Dynamic Ultrasound Spectrography (IDUS)—the Sequence

Figure 2:
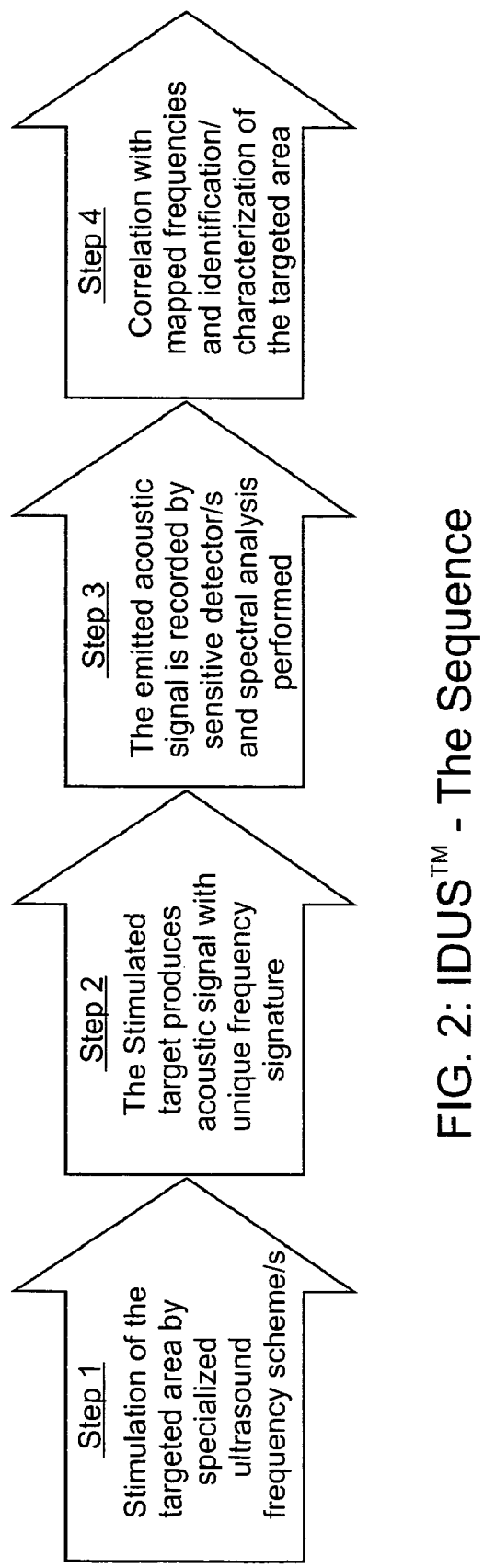
FIG. 2 is a flow diagram showing the sequence of the steps of the present invention IDUS technology.

Following the conventional ultrasound imaging, the Active Acoustics Approach uses multiple swept modulated beams at differential frequencies to stimulate the target (FIG. 2, Step 1). By projecting these beams onto the object, an oscillating radiation force is applied onto the object, which in return produces unique acoustic response signals (Step 2). The emitted acoustic signal is recorded by a sensitive detector or a series of detectors located in the vicinity of the targeted object (Step 3). The recorded response is subsequently analyzed and compared with pre-defined frequency maps for characterization and classification (Step 4).

Image-based Dynamic Ultrasound Spectrography (IDUS) is a platform technology that utilizes dual-mode imaging and spectroscopy to offer a real-time, bi-modal methodology based on non-invasively imaging of the area of interest (AOI), and A) Stimulating the AOI with specialized ultrasound-based waveform schemes,
B) Performing spectral analysis of the target's response to external stimulation,
C) Correlating the response with pre-existing frequency maps and identifying the target, and
D) Navigating and positioning of the AOI in 3-dimension.

Identification of the target is performed according to its characteristic peak response frequency signature, which is unique to its mechanical and material properties (viscosity, elasticity, plasticity, visco-elasticity, etc). Based on the recorded acoustic fingerprint, the target is classified in different categories of frequency bands. In Image-based Dynamic Ultrasound Spectrography (IDUS), each of the defined categories is investigated by sweeping the modulated ultrasound energy imposed onto the target in each frequency band. The response frequency could deviate from a few Hz to several tens of KHz and the response could be in the form of a narrow peak or a band of frequencies, based on the mass density and stiffness coefficient of the targeted area/material. A combination of Image-based Dynamic Ultrasound Spectrography (IDUS), and other modalities for measuring the elasticity of the targeted area will provide a complete and unique methodology for breast screening. For example, early detection of microcalcification in breast tissue (<100 micrometers typical dimension) and an assessment of the elasticity/stiffness of the AOI will provide important diagnostic information on the existence of premalignant lesions in the breast.

Presenting the Image-Based Dynamic Ultrasound Spectrography (IDUS) System for Breast Microcalcification Detection Image-based Dynamic Ultrasound Spectrography (IDUS) has been designed to either stand alone as a dual-mode ultrasound platform for screening and diagnosis or be integrated to and perform in conjunction with a standard ultrasound imaging platform. The Image-based Dynamic Ultrasound Spectrography (IDUS) system uses the assignee's proprietary ultrasound technology to stimulate the area of interest (AOI) in the breast and subsequently spectrally analyzes and characterizes the response frequency of the targeted area in search for microcalcification based on spectrography techniques. The dual-mode platform technology may utilize state-of-the-art ultrasound platforms and acoustic technologies for imaging, stimulating, frequency recording and localizing the AOI. Real-time spectral analysis determines the target's particular spectral response signature corresponding to its state.

Figure 3:
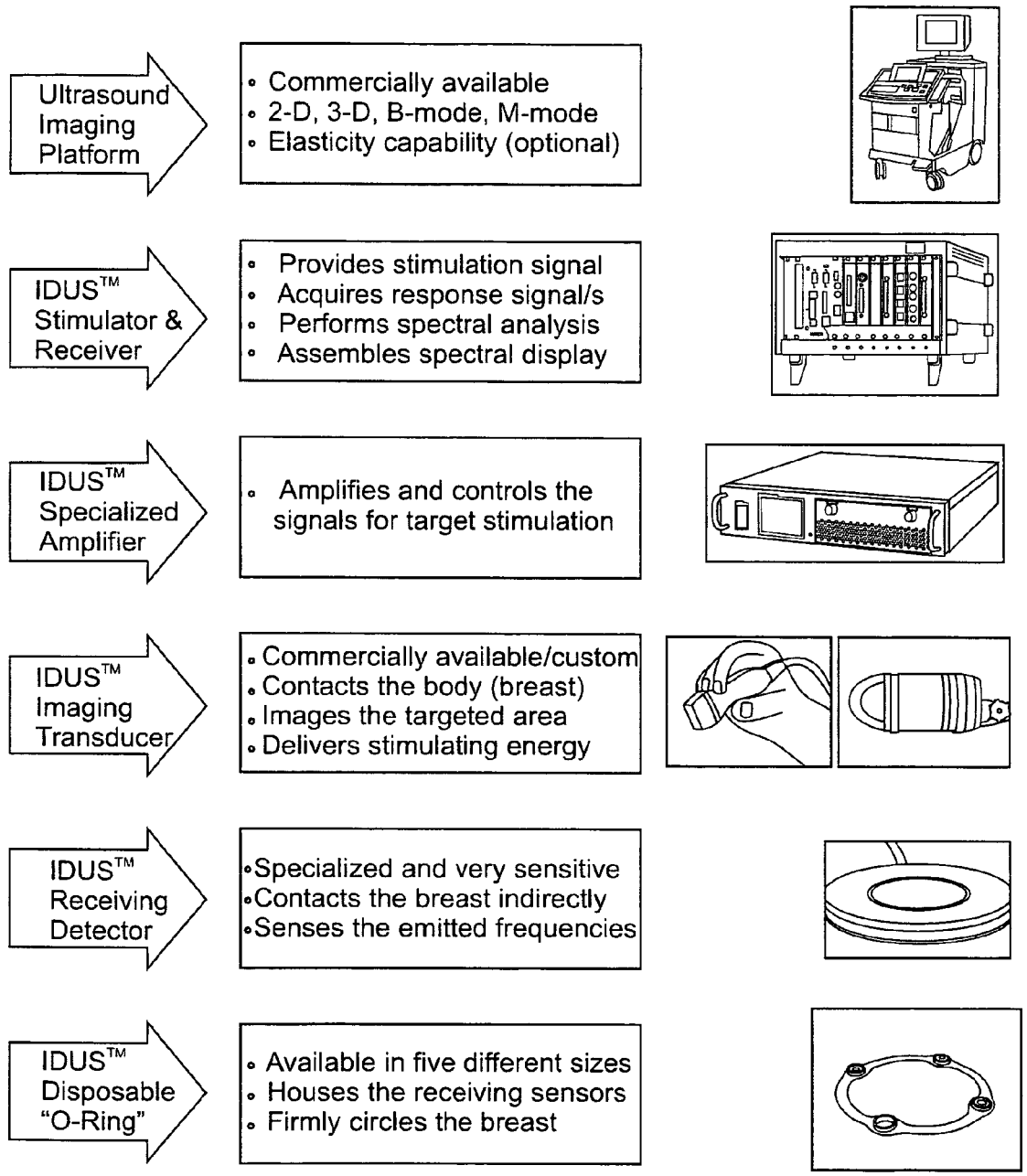
FIG. 3 is a flow diagram and pictures of the components utilizing the present invention IDUS technology.

Using the Image-based Dynamic Ultrasound Spectrography (IDUS) system, detection of breast micro-calcification (<100 micrometer) will be done during a routine clinical ultrasound examination providing additional quantitative information (stored in individual libraries for every patient). Since the examination is cost-effective and does not expose the examinee to any ionizing radiation whatsoever, it can be repeated on a more frequently basis (if required) for guidance, more effective follow-ups and selection of treatment/s. The components of the Image-based Dynamic Ultrasound Spectrography (IDUS) system for breast screening are described in the FIG. 3. In addition to the software for stimulation scheme, data analysis and processing and 3-D navigation, the most important hardware components of the Image-based Dynamic Ultrasound Spectrography (IDUS) system are: 1) the specialized power amplifier, 2) the sensors and 3) the modified imaging transducer. The power amplifier is an integral part of any standard ultrasound platform which may be modified to meet Image-based Dynamic Ultrasound Spectrography (IDUS) specifications. The sensors have to be custom-made to meet the sensitivity requirements for the range of emitted frequencies from breast microcalcifications. The only modification to the imaging transducer is related to the 3-D localization capability of the Image-based Dynamic Ultrasound Spectrography (IDUS) system. Other devices required for implementation of the Image-based Dynamic Ultrasound Spectrography (IDUS) system are standard components of any ultrasound platform and can be accommodated within the platform itself. These include: A) electronic filters, B) high-speed processors, C) computational capabilities, D) display monitors E) video cards.

It is important to note, that the Image-based Dynamic Ultrasound Spectrography (IDUS) system also includes a disposable "O-ring", made out of biocompatible material, available in different sizes to accommodate different anatomies (i.e., x-small, small, medium, large and x-large) and houses four sensors. The ring stably surrounds the breast by biocompatible adhesive material prior to the examination, facilitating the sensors to firmly couple with the breast skin via a thin biocompatible film. The film will prevent formation of an air gap between the sensor and the skin, thus enhancing returned data acquisition and eliminating the possibility of signal attenuation or distortion. It is expected that two rings will be used for screening two breasts in one examinee.

How does it Work?

Figure 4:
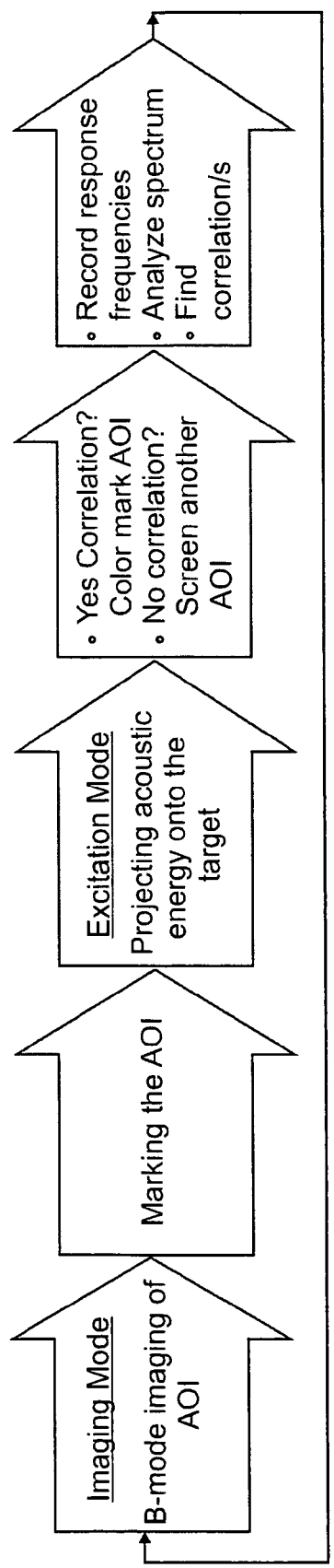
FIG. 4 is a flow diagram showing the process of the present invention in breast screening.

Imaging Mode—The imaging feature of an ultrasound system provides a 2 or 3-dimensional B-mode (grayscale) image of the targeted area (commonly performed during any routine procedure), FIG. 4. The image is obtained by using a linear-array transducer with a center frequency ranging from 1.0 megahertz (MHz) to 14 MHz depending on the application and depth of the AOI. Higher frequency provides imaging of smaller depth. For example, a 3 MHz transducer can provide images at depth of 12 to 15 centimeters in the body, whereas a 14 MHz transducer (typically used in pediatric applications or in breast imaging) can provide images of targets at approximately 1.5 centimeters depth. The grayscale imaging resolution of the advanced ultrasound platforms are reasonably high and thus their improved mapping capabilities.

Stimulation Mode—Once the grayscale image of the targeted area (any cross sectional scanned area) has been obtained and AOI marked, the procedure is switched to the stimulation mode where the AOI is projected with specific swept modulated sequential stimulation scheme/s delivered by Image-based Dynamic Ultrasound Spectrography (IDUS) via the same imaging transducer. By projection of the modulated stimulation scheme/s onto the target, an oscillating radiation force is generated that sets the object to motion or vibrate at a given frequency. The resulting motion or vibration produces sound signals (a unique signature), which is received by a series of receiving sensors positioned on the body (i.e., breast) in the vicinity of the ultrasound imaging scanner. A typical receiver is about 20 millimeters (or less) in diameter. The emitted frequencies may vary from a few Hz to several tens of KHz depending on the physical nature of the stimulated target.

Image-based Dynamic Ultrasound Spectrography (IDUS) spectrally analyzes the recorded signals in real-time to identify maximum emitted frequencies. The maximum peak of the frequency spectrum is then compared to a pre-defined map of frequencies corresponding to a potential targeted area (i.e., microcalcification). The pre-defined frequency map can be programmed into the ultrasound platform software. When a correlation between the recorded peak frequency and the programmed frequency map is found, the AOI on the B-mode image is colored according to a programmed color-coded scheme. The procedure is then switched back to the imaging mode and another area is screened and the sequence is repeated. A specific frequency map has been developed for each medical application of the Image-based Dynamic Ultrasound. Spectrography (IDUS) platform technology (breast, cardiac, orthopedic, etc.) and embedded into the ultrasound imaging platform database. The transition between different applications of Image-based Dynamic Ultrasound Spectrography (IDUS) is expected to be straightforward and will essentially be the same as done at present.

Image-Based Dynamic Ultrasound Spectrography (IDUS) Possesses a Number of Unique Advantages:

Non-invasive detection of structural differences in a targeted area can be achieved based on spectral analysis of the response frequency as a result of external stimulation—The characteristics of the vibrations of various targets (breast microcalcification, stress fractures, fractures in implanted mechanical devices, injured knee cartilage, muscle infract, catheters, contrast agents, etc.) and resultant sound signals are different and distinguishable in different material and mediums. Thus, detection and classification of unique frequency signatures allows differentiation and diagnosis of mechanical characteristics.

Real-time imaging—Saves on time-consuming image acquisition and post-processing, and especially streamlines guided biopsy and surgery.

High sensitivity and specificity—Different targets have different and yet specific frequency response signatures corresponding to their state. These will result in enhanced sensitivity and specificity of the IDUS™ technology.

User intuitive—The system is based on common ultrasound screening technology. Therefore, no complex or extraordinary training is required.

No ionizing radiation—IDUS™ allows frequent screening of populations at high risk, and frequent treatment follow-ups, with no hazard of radiation involved in X-ray based screening modalities.

Low cost capital equipment—The system is based on conventional ultrasound imaging technology, and will be marketed by ultrasound manufacturers as a standalone system or as an integral part of a high-end ultrasound platform at acceptable premium price.

High accessibility for patient follow-up—The IDUS™ system will be potentially available in every hospital, field and clinical setup currently hosting ultrasound equipment. Additionally, it may be used in operating rooms, field hospitals and rural areas without a need for major real-estate and special infrastructure.

Cost-effective treatments—The reimbursement cost of the new modality is expected to be much lower than competing functional imaging modalities such as MRI.

Multiple applications—For example, breast, cardiac, orthopedic, cranial, abdominal, etc.

3-D positioning—A unique advantage of the IDUS™ system which will allow for better imaging when combined with 3-dimensional ultrasound capabilities or for better positioning and localization of the AOI by using GPS compatible technologies.

Table 1 compares the IDUS™ technology with leading imaging technologies (currently available for breast screening or under development) according to several critical success factors. Note that complete information on some of the new modalities under development is not readily available and thus, the evaluation presented in this Table has been done based on preliminary assessments and estimations. For instance, the opto/thermo acoustic technologies have yet to be introduced to the market and proven practical and reliable. Their true evaluation will be possible following initial employment in clinical settings.

Introducing the Image-Based Dynamic Ultrasound Spectrography (IDUS) Breast Screening Application Image-based Dynamic Ultrasound Spectrography (IDUS) imaging screening and diagnostic technology will provide a safe, cost-effective, and reliable methodology with no ionizing radiation that can accurately detect small areas of microcalcifications (<100 microns) in breast based on their characteristic emitted frequencies.

How does it Work in Breast Screening?

Referring to FIGS. 4 and 5 and subfigures 5A through 5I, the Image-based Dynamic Ultrasound Spectrography (IDUS) procedure is carried out according to the following steps:

1. The patient is asked to lie supine on the examination bed.
2. A disposable and compliant O-ring will be placed around the breast, leaving the center portion available for the ultrasound r/scanner. The disposable O-ring has four housing openings for the receiving sensors, which are spaced 90 degrees apart. In each O-ring there is received a reusable sensor designed to be placed within a respective housing. A perspective view of a reusable sensor is shown in FIG. 5B.
3. Four small (round, approximately 20 mm in diameter) and sensitive reusable sensors will be placed into their designed housings around the O-ring (Step 2). Once in their housing, the sensors will be coupled with a thin and transparent film as illustrated in FIG. 5C, which will be firmly coupled with the skin by a layer of biocompatible adhesive surrounding the opening. Referring to FIG. 5D, the disposable O-ring with the sensors in place is located above the breast and thereafter as shown in FIG. 5E is positioned on the breast and affixed to the breast by removable adhesive around the bottom of the disposable O-ring as well as adhesive on the thin transparent film so that the disposable O-ring is firmly positioned on the breast during the scanning procedure.
4. Referring to FIGS. 5F to 5I, the B-mode ultrasound scanner will then scan each of the four quadrants of the breast looking for AOI with potential micro-calcification. The transmitted ultrasound frequency can be varied from 1-14 MHz covering a range of depths. The automatic frequency transition is a standard feature of the advanced ultrasound platforms to date. Once located, the scanner will remain steady, the B-mode image will be switched to "Freeze" mode and the AOI marked. AOI will be then stimulated by a swept band of modulated ultrasound frequencies generated by proprietary sequence of specialized schemes via the same ultrasound imager/scanner.
  4.A. FIG. 5F shows a perspective view showing the disposable O-ring and the receiving sensors positioned on the breast and an ultrasound scanner scanning the breast.

The B-mode ultrasound image is generated. FIG. 5G is a perspective view showing the device in its stimulation mode and stimulating signals transmitted by the ultrasound B-mode scanner toward the area of interest. FIG. 5H is a perspective view showing the ultrasound scanner transmitting sweeping frequencies in search for a peak response frequency from the area of interest. The disposable O-ring is attached to the breast and the receiving sensors sense the response frequencies emanating from the area of interest. The detected response frequency will reach a peak when an area of micro-calcification of a certain mass is detected. Finally, FIG. 5I shows that the recorded response frequency reaches a peak indicating an area with certain micro-calcification mass detected within the breast. The detected area of micro-calcification is then marked on the B-mode image according to a pre-defined color-code scheme and subsequently, the exact three-dimensional position of the area with micro-calcification is determined and marked on the B-mode image and recorded for future follow-ups.

5. When microcalcification is present, it will be stimulated by the sequential stimulation schemes, resulting in emitted characteristic response proportional to its mass. The response will be monitored in real-time and will appear as a spectrum where the peak frequency will be recorded and spectrally analyzed. Preliminary experiments with Image-based Dynamic Ultrasound Spectrography (IDUS) used in breast phantoms have indicated that the emitted frequencies from targeted soft tissues can vary from 50-200 Hertz (Hz), whereas corresponding emitted frequencies from a microcalcification site are estimated to be in the range of 1 KHz to 100 KHz.

6. If the recorded response correlates with a pre-defined frequency database, the marked AOI on the B-mode image is colored according to a particular color-coded scheme similar to velocity classification in ultrasound color-Doppler flow mapping.

7. Using specialized localization software, the 3-dimensional position of the AOI is determined based on the signals received by the receiving sensors and analyzes respectively. The exact 3-D position of the targeted area will be displayed in the B-mode image and marked on a separate reference device for future reference.

Four round reusable sensors (receivers) are firmly housed at 90 degrees apart on the O-ring. Three of the sensors would determine the X-Y-Z coordinates of the exact location of the micro-calcification within the breast. The forth sensor is used for correcting any errors in determining the X-Y-Z coordinates by the other three sensors. Another such sensor is positioned within the imaging scanner and used to provide a reference vertical axis (FIGS. 6A and 6B) to: 1) determine the depth of the micro-calcification sites and 2) relative to which the said X-Y-Z coordinates are determined. In the present invention, this vertical axis is important to ensure that the positioning of micro-calcifications within the breast is performed irrespective of the geometry changes that may occur in the breast at different times and between one examination to the other.

Competing Imaging Technologies

Table 2 presents the competition among imaging technologies, their strengths and weaknesses when compared to IDUS™ technology.

TABLE 1

IDUS ™ Technology Compared with Leading Diagnostic Imaging Modalities

| | Imaging Technology | | | | | |
|---|---|---|---|---|---|---|
| | IDUS ™ | Imaging Ultrasound | X-ray Mammography | CT | MRI | Opto/Thermo Acoustics* |
| Principle | Ultrasound | Ultrasound | X-ray | X-ray | Magnetic Field | Light/Laser |
| Penetration Depth | ≦20 cm | ≦20 cm | Whole | Whole | Whole | ~5 cm |
| Real-Time | Yes | Yes | Yes | No | No | No |
| Sensitivity | ≦100 μm | ≦200 μm | ≦100 μm | ≦100 μm | ≦100 μm | ~5 mm |
| Dual-Mode | Yes | No | No | No | Yes | No |
| Ionizing Radiation | No | No | Yes | Yes | No | No |
| Interventional | Yes | Yes | Yes | No | No | No |
| Cost | Low | Low | Low | High | High | Low** |
| Market | DIC & PO | DIC & PO | DIC | DIC | DIC | DIC |
| DIC/PO | | | | | | |

*These techniques have yet to demonstrate data reproducibility and practicality in clinical settings
**The cost of the opto/thermo acoustic techniques is unknown and the evaluation has been done based on initial assessments
DIC—Diagnostic imaging center
PO—Physician office

TABLE 2

Competing Imaging Technologies

| Technology | Strengths | Weaknesses | Selected Manufacturers |
|---|---|---|---|
| IDUS ™ | Bi-modal, image guided excitation of the target Provides real-time qualitative image of the targeted area and | Frequency dependent penetration depth Requires certain hardware modifications of conventional | BioQuantetics, |

TABLE 2-continued

Competing Imaging Technologies

| Technology | Strengths | Weaknesses | Selected Manufacturers |
|---|---|---|---|
| | quantitative data about the structural integrity of the targeted area. 3-D GPS-like positioning capability Non-invasive No ionizing radiation Safe Reliable Cost-effective Not Doppler based Portable Suitable for field applications Suitable for operating room applications | ultrasound platforms Requires an specialized power amplifier | |
| X-Ray Mammography | Used in mammography and is the only FDA approved technology for cancer detection. High penetration depth Low cost High resolution Real time imaging | Affected by tissue density X-ray radiation Requires special setting Allows for morphologic imaging only | Eastman Kodak Fischer Imaging GE Healthcare Medical Systems Lorad Corporation Philips Siemens Barco Hologic Dalsa Life Sciences |
| MRI | High resolution Detailed images of the soft-tissue structures High penetration depth Allows for morphologic, as well as functional imaging | The most expensive imaging technology Requires special setting Cannot detect calcium present in a tumor Image degradation due to motion artifact effects | Fonar Corp. GE Healthcare Hitachi Philips Siemens Toshiba |
| 2/3-Dimensional Ultrasound | High Resolution Real-Time qualitative image of the targeted area Does not require special logistics, real-estate or settings No ionizing radiation Non-invasive No ionizing radiation Safe Cost effective Portable | Medium penetration depth Allows for morphologic imaging only Low specificity | B-K Medical Siemens GE Healthcare Medison Co. Philips Shimadzu Aloka Hitachi Terason Toshiba |
| CT | High penetration depth High resolution Identify normal and abnormal structures | Not real-time High Cost Ionizing radiation Requires special setting Allows for morphologic imaging only | Shimadzu Corp Schaerer Mayfield Siemens Toshiba GE Healthcare Medrad Xoran Technologies Prism Microsystems Philips |
| Digital Mammography | High Penetration depth Real Time Display of sections as thin as 1 mm Allows for detection of cancer hiding within overlapping tissue | Ionizing radiation Requires special logistics and settings High cost Short life span | GE Healthcare Siemens Hologic |
| Nuclear Imaging | High penetration depth Allows for functional imaging | Medium resolution Radiation Requires special settings Medium Costs Time consuming | Positron Corp. Naviscan PET Systems Transphoton GE Healthcare Siemens Syntermed Philips Toshiba Ultraspect Hamamatsu Photonics |

TABLE 2-continued

Competing Imaging Technologies

| Technology | Strengths | Weaknesses | Selected Manufacturers |
|---|---|---|---|
| Tomosynthesis | High resolution<br>3D imaging application<br>Low cost | Requires special setting<br>Short life span<br>Ionizing radiation | GE Healthcare<br>Siemens<br>Hologic |
| Digital Infrared Imaging | Detection of pre-cancerous state of the breast or the presence an early tumor that is not yet large enough to be detected by physical examination, mammography, or other types of structural imaging<br>No radiation<br>Non invasive<br>Real time | Requires special settings<br>Most Effective in detecting tumors that are close to the skin surface but not tumors deeper in the breast.<br>Not sensitive enough to detect small tumors or micro-calcification. | OptoSonics |

What is claimed is:

1. A non-invasive method of identifying microcalcification in a breast of a human body comprising:
   a. positioning a disposable biocompatible, circular and compliant ring on the breast (ring) which contains four housings spaced approximately 90 degrees apart on the ring and each housing retaining an acoustic receiving sensor which is positioned within the ring;
   b. each respective breast-facing surface of each respective sensor housing is open and retains a thin and acoustically transparent biocompatible plastic film which separates the receiving sensor from directly contacting skin on the breast;
   c. each respective breast-facing surface of the ring around the location of the receiving sensors is covered with biocompatible adhesive material coupled with a removable protective material selected from the group consisting of paper or plastic material;
   d. the biocompatible adhesive material is exposed by removing the protective paper or plastic material;
   e. positioning the disposable ring on and around a human breast and adhering the ring onto the breast so that the sensor housings and the thin film are firmly coupled with the skin of the breast and located at positions approximately 90 degrees apart;
   f. utilizing a bi-modal Image-based Dynamic Ultrasound Spectrography system with "Imaging Mode" and "Stimulation Mode";
   g. the Image-based Dynamic Ultrasound Spectrography system is switched to its "Imaging Mode";
   h. an ultrasound imaging transducer is utilized to scan different segments of the breast and impact the breast with ultrasound imaging frequencies in the range of 1 megahertz (MHz) to 14 MHz to image the breast at each given time;
   i. an ultrasound B-mode gray scale image is created in real-time whereby ultrasound frequencies are transmitted towards specific segments of the breast and subsequently reflected from the specific segments of the breast towards the transducer;
   j. while the transducer is still in the imaging mode, the Image-based Dynamic Ultrasound Spectrography system is switched to its "Stimulation Mode";
   k. the selected segment of the breast is stimulated by an ultrasound modulated scheme of non-invasive stimulation sequence in the form of a fixed band of frequencies or a derivative of which, as a swept band of frequencies, delivered by said ultrasound imaging transducer;
   l. when the stimulation sequence is delivered as a swept band of frequency, one signal generator provides incremented frequency ranges while another signal generator provides a fixed frequency so that due to instantaneous differences in the frequencies from the signal generator, certain acoustic radiation forces are generated proportional to the characteristic response frequencies of targeted microcalcifications that stimulate and vibrate the targeted microcalcifications;
   m. a single stimulation sequence is broken down into different segments so that the frequency scan occurs in a particular and controlled sequence called "one presentation" so that the swept band of frequencies can be applied over the desired frequency spans, thereby exerting the intended radiation force and in turn, creating the response in the targeted microcalcifications while minimizing the time for which each frequency span is introduced, which in turn increases the signal-to-noise ratio (S/N);
   n. when the stimulation sequence is delivered as modulated fixed band of frequencies, the data is acquired over a time interval wherein a fixed megahertz frequency is applied to the targeted microcalcifications and another variable and swept band of megahertz frequencies is incremented;
   o. in detection of stationary breast microcalcification, said modulated fixed band of stimulation frequencies is preferred wherein a first-hand estimate of the response is obtained and then a subsequent derivative of a swept band of megahertz frequencies is applied;
   p. in either the fixed band of frequency scheme of the swept band of frequency scheme, the stimulating signal is swept over a band of Hertz or kilohertz range frequencies and the frequencies are modulated on the megahertz ultrasound carrier frequency;
   q. as a result of stimulation, the microcalcifications produce response frequencies in the form of acoustic signals corresponding and specific to their mass density and structure and that are received by the receiving sensors positioned on the ring around the breast;
   r. utilizing an acoustic readout apparatus whereby certain frequencies are received by one or more of the acoustic receiving sensors positioned on the disposable ring;

s. the detected frequencies received by each receiving sensor are compared and correlated with a predetermined map of peak frequencies corresponding to different microcalcification sizes, mass densities and structures;

t. if a detected (received) frequency received by sensor/s correlates with a predetermined frequency in a the predetermined frequency signature map, the targeted site on the B-mode image is color-coded using a predetermined color scheme and the exact coordinates of the site within the breast is determined and co-registered with the B-mode image based on the readout from each sensor using certain triangulation techniques; and u. incorporating a fifth sensor within the ultrasound transducer in the Image-based Dynamic Ultrasound Spectrography system, the fifth sensor creating a reference axis in conjunction with the four acoustic receiving sensors, the fifth sensor used to create a reference axis so that the relative location of a detected site can be marked and co-registered to determine an exact three-dimensional location.

2. The method in accordance with claim 1, wherein soft breast tissues which are impacted by an acoustic radiation force delivered by the modulated ultrasound frequency emit a response frequency of 1-50 Hz and microcalcifications emit frequencies in a range of 100 Hz to 100 KHz.

3. A non-invasive method to identify in a human breast comprising:

a. placing a disposable and compliant ring around the breast and leaving the center portion of the breast available for scanning and stimulation by an ultrasound transducer;

b. positioning four sensors on a disposable ring which is placed around and removably adhered to the breast, each sensor respectively coupled with a thin and acoustically transparent film which is firmly coupled to skin on the breast by a layer of biocompatible adhesive surrounding the thin film on the ring;

c. utilizing a B-mode ultrasound transducer to scan the breast creating a gray-scale B-mode image of the area of interest with potential microcalcifications;

d. a transmitted ultrasound imaging frequency band is used to cover a range of depths in the breast;

e. once a B-mode image of the area of interest in the breast is obtained, for the stimulation purposes the total area of interest or a portion thereof in the B-mode image is marked;

f. the selected area of interest is then targeted and stimulated by a swept band of frequencies generated by a proprietary sequence of specialized schemes delivered by said B-mode ultrasound imaging transducer;

g. when a mass is present, it is stimulated by sequential frequency schemes resulting in emanating a characteristic response frequency proportional to its mass, size density and structure;

h. monitoring the response in real time so that a spectrum including a peak response frequency is recorded and spectrally analyzed;

i. having a detected peak response frequency correlated with a predetermined database of predefined peak frequencies to determine presence of a specific mass;

j. if a detected response frequency or band of frequencies correlate with peak value or values in a predefined frequency signature map, the exact three-dimensional coordinates of the area from where the frequency or frequencies have been detected is marked, co-registered and integrated on the B-mode image and colored according to a particular predetermined color-coded scheme; and k. utilizing certain specialized positioning techniques, including but not limited to triangulation techniques, an exact three-dimensional position of an area of interest is determined based on signals received by receiving sensors and analyzers respectively, with an exact three-dimensional position of a targeted area co-registered and displayed on a B-mode image and recorded for future reference.

4. The method in accordance with claim 3, wherein frequencies of soft tissue of the breast are in the range of 1-50 Hz and response frequencies of microcalcifications are in a range of 100 Hz to 100 KHz.

5. The method in accordance with claim 3, further comprising incorporating a fifth sensor within the Image-based Dynamic Ultrasound Spectrography system, the fifth sensor used to create a reference axis in conjunction with the four acoustic receiving sensors, the fifth sensor used to create a reference axis so that the relative location of a detected microcalcification can be marked to determine the exact location.

6. A non-invasive method of identifying microcalcification in a breast of a body, comprising:

a. positioning a multiplicity of specialized acoustic receiving sensors on a sensor retaining apparatus so that the acoustic receiving sensors are spaced apart from each other;

b. positioning the sensor retaining apparatus on and around the breast so that the multiplicity of acoustic sensors is positioned on and around the breast;

c. utilizing a bi-modal Image-based Dynamic Ultrasound Spectrography system which has an Imaging Mode and a Stimulation Mode;

d. utilizing the Imaging Mode of the Image-based Dynamic Ultrasound Spectrography system with an ultrasound imaging transducer to scan different segments of the human breast and impact the human breast with a given range of ultrasound imaging frequencies to image the breast at given times to thereby create an ultrasound image wherein ultrasound frequencies are transmitted toward specific segments of the breast and subsequently reflected from each specific segment of the breast toward the transducer;

e. utilizing the Simulation Mode of the Image-based Dynamic Ultrasound Spectrography system with said ultrasound imaging transducer and stimulating selected segments of the breast by an ultrasound modulated non-invasive swept band of frequency schemes delivered by said ultrasound imaging transducer utilizing two modulated signals generated so that one signal provides the swept band of frequencies while the other signal provides a fixed ultrasound frequency so that due to instantaneous differences in applied frequencies, certain acoustic radiation forces are generated proportional to the characteristic response frequencies of targeted microcalcification so that the applied radiation forces stimulate and vibrate the targeted microcalcifications;

f. a single stimulation sequence is broken down into different segments so that the frequency scan occurs in a particular and controlled sequence called "one presentation";

g. a stimulation signal is swept over a band of Hertz or kilohertz range frequencies and the frequencies are modulated on a megahertz ultrasound imaging frequency so that the stimulated microcalcifications produce response frequencies in the form of acoustic signals corresponding and specific to their mass density and that are received by the receiving sensors positioned on the ring;
h. utilizing an acoustic readout apparatus so that certain frequencies are received by one or more of the sensors positioned on the disposable ring; and
i. comparing and correlating the received frequencies with a predetermined map of peak frequencies corresponding to different mass densities and structures so that when a detected frequency correlates with a predetermined frequency in a frequency signature map, a targeted site on the image is color-coded in real-time utilizing a predetermined color scheme and exact coordinates of the site within the breast is determined and co-registered with the ultrasound image based on the readout from each sensor using certain specialized positioning techniques, including but not limited to triangulation techniques.

7. The method in accordance with claim 6, further comprising the swept band of frequencies can be applied in real-time over the desired frequency spans, thereby exerting an intended radiation force and in turn, creating the response in the targeted microcalcifications while minimizing a time for which each frequency span is introduced, which in turn increases a signal-to-noise ratio (S/N).

8. The method in accordance with claim 6, further comprising incorporating an additional sensor within the Image-based Dynamic Ultrasound Spectrography system, the additional sensor used to, create a reference axis so that the relative locations of a detected microcalcification can be marked and determined.

9. The non-invasive method in accordance with claim 6 wherein exact coordinates of the site within the breast are determined based on readouts from each of the acoustic receiving sensors and utilizing certain specialized positioning techniques, including but not limited to triangulation techniques.

10. The non-invasive method in accordance with claim 6 wherein said sensor retaining apparatus is a circular compliant ring which contains spaced apart housings to respectively retain each of the multiplicity of acoustic receiving sensors.

11. The non-invasive method in accordance with claim 10, further comprising a multiplicity of acoustic receiving sensors each respectively placed in a housing wherein the housings are spaced apart.

12. The non-invasive method in accordance with claim 6 wherein each respective acoustic receiving sensor has a thin acoustically transparent biocompatible plastic film on the breast-facing surface of the ring to separate each respective acoustic receiving sensor from the skin on the breast.

13. The non-invasive method in accordance with claim 12, further comprising biocompatible adhesive material on each biocompatible plastic film.

14. The non-invasive method in accordance with claim 13 wherein each biocompatible adhesive material is covered by a removable protective material.

15. A non-invasive method of detecting in a breast of a body, comprising:
a. positioning a multiplicity of acoustic receiving sensors on a sensor retaining apparatus so that the respective acoustic receiving sensors are spaced apart from each other;
b. positioning the sensor retaining apparatus on and around the breast so that the multiplicity of acoustic sensors is positioned on and around the breast;
c. utilizing a bi-modal Image-based Dynamic Ultrasound Spectrography system which has an Imaging Mode and a Stimulation Mode;
d. utilizing the Imaging Mode of the Image-based Dynamic Ultrasound Spectrography system with an ultrasound imaging transducer to scan different segments of the human breast and impact the human breast with ultrasound imaging frequencies to image the breast at given times to thereby create an ultrasound image in real-time wherein ultrasound frequencies are transmitted toward specific segments of the breast and subsequently reflected from each specific segment of the breast toward the transducer;
e. utilizing the Simulation Mode of the Image-based Dynamic Ultrasound Spectrography system with said ultrasound imaging transducer and stimulating selected segments of the breast by a non-invasive modulated swept band of frequencies wherein a fixed megahertz frequency is applied to a targeted microcalcifications and another different megahertz frequency is incremented over a band of frequencies to obtain a first-hand estimate of the targeted microcalcifications based on the differences between the fixed and incremented frequencies;
f. a stimulation signal is swept over a band of Hertz or kilohertz range frequencies and the frequencies are modulated on a megahertz ultrasound frequency so that the microcalcifications produce response frequencies in the form of acoustic signals corresponding and specific to their mass density and structure and that are received by the acoustic receiving sensors positioned on the ring and read out by an acoustic readout apparatus; and
g. comparing and correlating the received frequencies with a predetermined map of peak response frequencies corresponding to different mass densities and structures so that when a detected frequency correlates with a predetermined frequency in a frequency signature map, a targeted site on the ultrasound image is color-coded in real-time utilizing a predetermined color scheme and exact coordinates of the site within the breast are determined and co-registered with the ultrasound image based on the readout from each sensor using certain specialized positioning techniques, including but not limited to triangulation techniques.

16. The method in accordance with claim 15, further comprising incorporating an additional sensor within the Image-based Dynamic Ultrasound Spectrography system, the additional sensor used to create a reference axis so that the relative locations of detected microcalcifications can be co-registered and determined.

17. The non-invasive method in accordance with claim 15, wherein exact coordinates of the site within the breast are determined based on readouts from each of the acoustic receiving sensors and utilizing certain specialized positioning techniques, including but not limited to triangulation techniques.

18. The non-invasive method in accordance with claim 15, wherein said sensor retaining apparatus is a compliant ring which contains spaced apart housings to respectively retain each of the multiplicity of acoustic receiving sensors.

19. The non-invasive method in accordance with claim 18, further comprising a multiplicity of acoustic receiving sensors each respectively placed in a housing wherein the housings are spaced apart.

20. The non-invasive method in accordance with claim 15, wherein each respective acoustic receiving sensor has a thin acoustically transparent biocompatible plastic film on the breast-facing surface to separate each respective acoustic receiving sensor from the skin on the breast.

21. The non-invasive method in accordance with claim 20, further comprising biocompatible adhesive material on each biocompatible plastic film.

22. The non-invasive method in accordance with claim 21 wherein each biocompatible adhesive material is covered by a removable protective material.

23. A non-invasive method to identify in a human breast, comprising:
   a. positioning a multiplicity of acoustic receiving sensors on a sensor retaining apparatus so that the acoustic receiving sensors are spaced apart from each other;
   b. positioning the sensor retaining apparatus on and around the breast so that the multiplicity of acoustic sensors are positioned on and around the breast and leaving the center portion of the breast available for scanning and stimulation by an ultrasound transducer;
   c. utilizing the ultrasound transducer to image breast creating an ultrasound image of the area of interest with potential microcalcifications;
   d. the transmitted ultrasound imaging frequency band covers a range of depths in the breast;
   e. once an image of the area of interest in the breast is obtained by the ultrasound transducer, whether maintained stationary or moving over the breast, the total area of the breast or a segment thereof in the ultrasound image will be marked;
   f. the marked area of interest is then stimulated by a modulated swept band of frequencies generated by proprietary sequence of specialized schemes delivered by said ultrasound transducer;
   g. when a microcalcification is present, it is stimulated by a sequence of modulated frequency schemes resulting in emanating a characteristic response frequency proportional to its size, mass and structure;
   h. monitoring a response in real time so that a spectrum including a peak response frequency is recorded and spectrally analyzed; and
   i. having a detected peak response frequency correlated with a predetermined database of peak response frequency maps to determine and verify presence of a specific mass.

24. The method in accordance with claim 23, utilizing an additional sensor to create a reference axis so that the relative location of a detected microcalcification can be marked and co-registered to determine an exact three-dimensional location.

25. The non-invasive method in accordance with claim 23, wherein said sensor retaining apparatus is a compliant ring which contains spaced apart housings to respectively retain each of the multiplicity of sensors.

26. The non-invasive method in accordance with claim 25, further comprising a multiplicity of acoustic receiving sensors each respectively placed in a housing wherein the housings are spaced apart.

27. The non-invasive method in accordance with claim 26, wherein each respective acoustic receiving sensor is reusable.

28. The non-invasive method in accordance with claim 27, wherein each reusable sensor has a thin acoustically transparent biocompatible plastic film on the breast-facing surface to separate each respective acoustic receiving sensor from the skin on the breast.

29. The non-invasive method in accordance with claim 28, further comprising biocompatible adhesive material on each biocompatible plastic film.

30. The non-invasive method in accordance with claim 29, wherein each biocompatible adhesive material is covered by a removable protective material.

31. The method in accordance with claim 23, wherein frequencies of soft tissue of breast are in a range of 1-50 Hz and the response frequencies of microcalcifications are in a range of 100 Hz to 100 KHz.

32. The method in accordance with claim 23, further comprising:
   a. if the detected response frequency or band of frequencies correlate with peak value or values in a predefined frequency signature map, the exact three-dimensional coordinates of the area from where a frequency or frequencies have been detected is marked and co-registered on the ultrasound image and colored according to a particular predetermined color-coded scheme; and
   b. utilizing certain specialized positioning techniques, including but not limited to triangulation techniques, an exact three-dimensional position of an area of interest is determined based on signals received by receiving sensors and analyzers respectively, with an exact three-dimensional position of a targeted area co-registered and displayed on the ultrasound image and recorded for future reference.

33. The non-invasive method in accordance with claim 23, further comprising the acoustic receiving sensors are disposable.

* * * * *

UNITED STATES PATENT AND TRADEMARK OFFICE
CERTIFICATE OF CORRECTION

PATENT NO. : 8,376,947 B2  
APPLICATION NO. : 12/079272  
DATED : February 19, 2013  
INVENTOR(S) : Edmond Rambod et al.

Page 1 of 1

It is certified that error appears in the above-identified patent and that said Letters Patent is hereby corrected as shown below:

In The Claims

Col. 19, lines 27-28 should read --

3.    A non-invasive method to identify microcalcification in a human breast comprising:

Col. 21, lines 56-57 should read --

15.    A non-invasive method of detecting microcalcification in a breast of a body, comprising:

Col. 23, lines 7-8 should read --

23.    A non-invasive method to identify microcalcification in a human breast, comprising:

Signed and Sealed this  
Tenth Day of May, 2016

Michelle K. Lee  
*Director of the United States Patent and Trademark Office*